United States Patent [19]
Mackta

[11] 3,932,938
[45] Jan. 20, 1976

[54] PIGMENT PACKAGE FOR DENTAL FILLING MATERIALS

[76] Inventor: Leo Mackta, 444 Beach 132nd St., Belle Harbor, N.Y. 11694

[22] Filed: Dec. 11, 1972

[21] Appl. No.: 313,758

[52] U.S. Cl. .................................................. 32/15
[51] Int. Cl.² ........................................... A61K 5/02
[58] Field of Search ......... 32/39, 1, 15, 71; 206/1.7, 206/1.8, 83; 35/26, 28.3, 28.5

[56] References Cited
UNITED STATES PATENTS

| | | | |
|---|---|---|---|
| 1,137,482 | 4/1915 | Hanly | 32/39 |
| 2,711,605 | 6/1955 | Dripps | 206/1.7 |
| 2,963,797 | 12/1960 | Mueller | 35/26 |

Primary Examiner—Robert Peshock

[57] ABSTRACT

A pad of sheets each containing a plurality of discrete, premeasured quantities of pigments for producing natural colors in composite plastic dental filling materials, said pigments being adhered to said sheets by a hardened vehicle in which said pigments are dispersed, and said pigments in said vehicle being directly dispersible in said filling materials when brought into contact therewith.

9 Claims, 2 Drawing Figures

PIGMENT PACKAGE FOR DENTAL FILLING MATERIALS

BACKGROUND OF THE INVENTION

There is a group of plastic dental filling materials called "composites". These consist of two components, a base and a catalyst which must be mixed together immediately prior to insertion in a cavity in a tooth. Various fillers are incorporated in one or the other of the components to add certain properties to the composite. Materials like powdered quartz or other silicates add resistance to wear and increase translucency. Pigments or opacifiers are added to the composite to enable closer color matches to the natural teeth.

The two components come in varying physical states. They may each be pastes, powder and liquid, and one brand uses a paste for the base and incorporates the catalyst into the sheets of the disposable paper mixing pads.

Practically all the brands supply disposable pads of paper, usually glazed, upon which the portions of base and catalyst are mixed together with a disposable plastic spatula. Except for the one brand described above, where the catalyst is impregnated into the mixing paper, the paper serves only the mechanical purpose of supplying a smooth expendable mixing surface.

The companies supply the composites in various shades which will match the gamut of colors found in natural teeth. Blending may be performed by the dentist among the various colors in order to obtain a better color match. Usually three or four basic shades will be adequate to match the majority of teeth.

SUMMARY OF THE INVENTION

It is a feature of the present invention that the components of a composite filling material, for example, a paste base and a paste catalyst be formulated in a very light shade. Each sheet of paper in the mixing pad for this system will then have printed on it, in a small region, areas of non-toxic pigment in a non-toxic carrier medium or vehicle. This printing may be in any shape or figure, but most desirably in columns or triangular wedges or groups of dots, each column or wedge or groups of dots being printed in one of the basic colors required for matching the colors of natural teeth.

In use, the dentist selects the proper shade of the natural tooth with a conventional shade guide, which additionally will indicate the proportions of the required pigments to be used for the measured amount of composite material. One of the components, which will either leach out or dissolve the pigment from the printed area, or the component with the hard filler which will mechanically rub the printed area to release the pigment, is spatulated over a predetermined area of the printing to absorb the pigment. The portion of the component may now be shifted to a differently colored printed area for further blending if required. The resultant mixture may be compared directly with the tooth, so that in the experience of the dentist he may judge what the final shade will be when the complete mixture is made.

The two components are now finally spatulated together on a non-printed region of the paper sheet, as heretofore, and the filling inserted. The sheet is then torn off the pad as usual, and discarded.

DESCRIPTION OF THE PREFERRED EMBODIMENT

Figure 1:
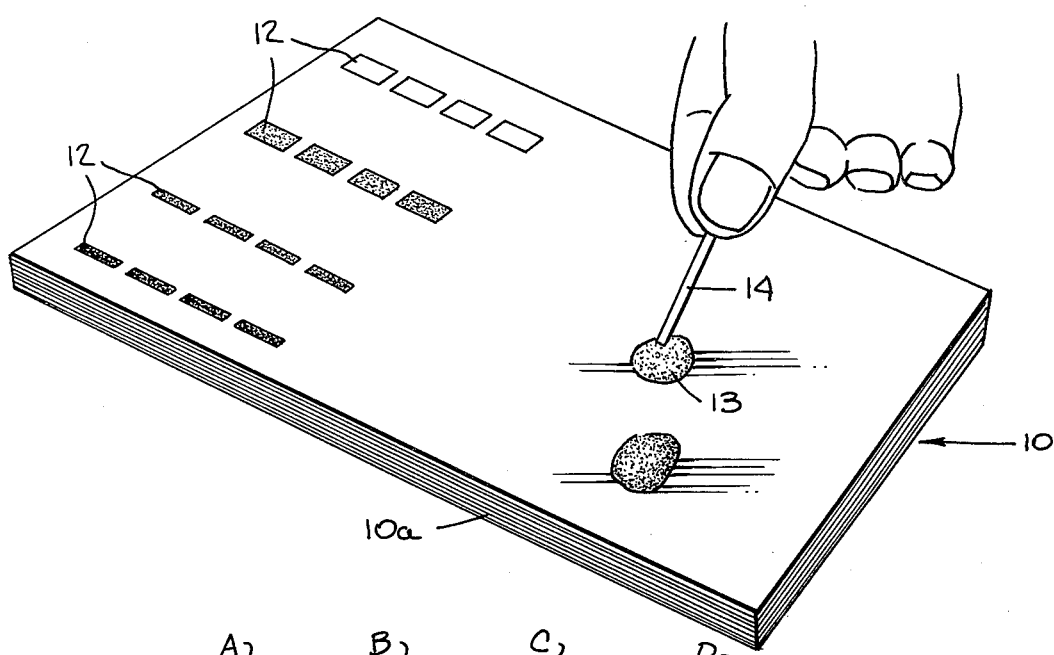
FIG. 1 is an isometric view of one embodiment of the invention.
Figure 2:
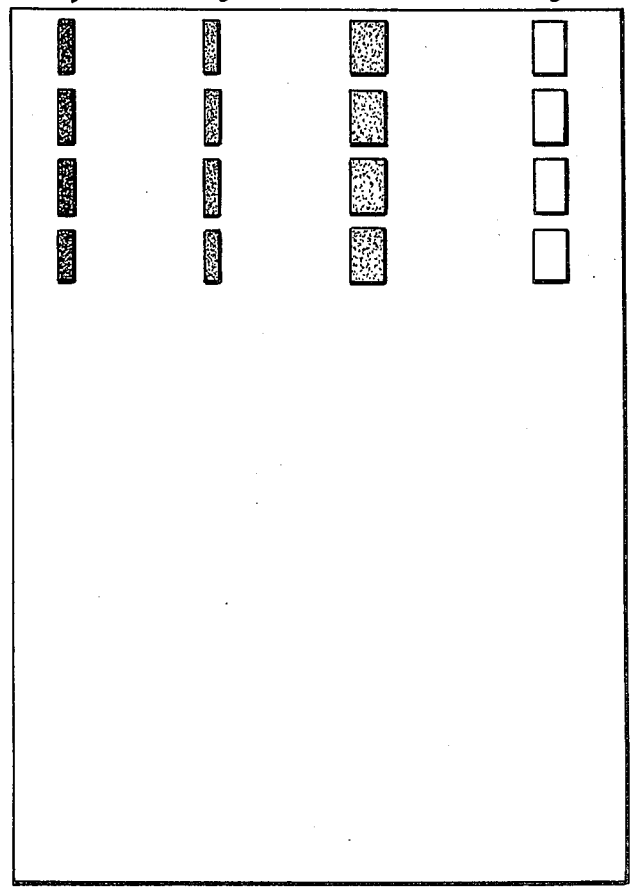
FIG. 2 is a plan view of the embodiment shown in FIG. 1.

Referring to the drawings, a preferred embodiment is shown in which a pad containing a plurality of sheets is designated generally by reference numeral 10. Each sheet 10a has imprinted or otherwise affixed to one surface 11 thereof a plurality of pigmented portions 12. As shown the pigmented portions are distributed in rows of individual segments of different measured amounts, the segments in a given row each containing equal amounts of a given pigment or dye and the quantities of one dye being specifically different from those of another dye, depending on the particular dye involved and the usual quantity used. By way of example the segmented portions in row A would be blue pigment, in row B brown, row C yellow and row D opaque white.

It is preferred that the printed portion of each sheet containing the pigments be substantially smaller in area than the unprinted portion so that there will be ample room to mix and blend the components on the latter portion.

Each pigment is added to a vehicle which is then adhered to the card 10 by any conventional technique such as printing. As an example the formula for 100 grams of vehicle is as follows:

| | |
|---|---|
| Methyl methacrylate (polymer) | 4.2 gm |
| Aerosil (R 972 manufactured by De Gussa, Inc., New York, N.Y.) | 3.5 gm |
| Methyl ethyl ketone | 92.3 gm |

Another formulation for the vehicle may be as follows:

| | |
|---|---|
| Bisphenol A | 15.0 gm |
| Methyl methacrylate (polymer) | 1.0 gm |
| Aerosil (R 972 manufactured by De Gussa, Inc., New York, N.Y.) | 4.0 gm |
| Methyl ethyl ketone | 80.0 gm |

The Aerosil is added to the methyl ethyl ketone, then the methacrylate added to that mixture. By way of example the weight of pigments to be added to the 100 grams of vehicle may be as follows: (All pigments are supplied by H. Kohnstamm & Co., Inc.)

| | | |
|---|---|---|
| Yellow | - | 7.0 gm iron oxide ochre No. 3506 |
| Opaque white | - | 10.0 gm titanium dioxide |
| Brown | - | 5.0 gm of mixture (by weight): 1.0 part ochre No. 3506; 2.0 part, red oxide No. A 6205; and 0.4 part black oxide No. A 8214 |
| Blue | - | 2 gm black oxide No. A 8214; and 0.2 gm D and C Blue No. 6 |

In use, with the aid of a shade guide the dentist estimates which pigments are necessary and approximately how much of each is required to obtain a plastic filling material having the same color as the tooth being filled. One component is spatulated over the required length of pigment print on the top sheet of the pad, removing a segment or fraction of a segment completely from the paper, and is mixed by a spatula 14 or other convenient means. The colored base material is held against the tooth to judge the match, and any correction is made either by spatulating in another portion of the print or diluting the mix with more of the same component.

For those composite brands which use two paste components, the first component is returned to the pad after the proper match is obtained, and another portion of pigment equal to the length previously used, is spatulated into it. This doubles the concentration of pigment, so that when an equal portion of the second component is finally spatulated with the first, the color is diluted back to the original proper match. The mix is then ready for insertion into the tooth cavity.

The sheet 10 may be made of any suitable material such as plastic, cardboard, kraft paper or the like.

Each segmented portion of pigment may contain about 0.05 grams of pigmented material or other quantity as experience shows to be an average amount.

After the filling material has been formulated as described and put into the tooth, the used sheet is torn from the pad to expose the next printed sheet for use in a similar manner. The sheets may be rendered severable from the pad by any conventional means (not shown).

While one embodiment has been shown and described herein, it is to be understood by those skilled in the art that certain changes and additions may be made without departing from the scope and spirit of the invention.

I claim:

1. A sheet containing a plurality of discrete, premeasured quantities of pigments for producing natural colors in composite plastic dental filling materials, said pigments being adhered to said sheet by a hardened vehicle in which said pigments are dispersed, and said pigments in said vehicle being directly dispersible in said filling materials when brought into contact therewith.

2. A sheet according to claim 1 having a plurality of pigments disposed thereon in separate spaced apart rows, each row containing a separate pigment in segmented portions in columnar arrangement.

3. A sheet according to claim 2 in which there are four rows respectively containing pigments of yellow, brown, blue and opaque white.

4. A sheet according to claim 2 in which said portions are wedge-shaped and each portion contains about 0.05 grams of material.

5. A sheet according to claim 2 in which said segmented portions are rectangular and contain up to about 0.05 grams of material.

6. A sheet according to claim 2 in which said portions are distributed as a series of dots and contain about 0.05 grams of material for each color.

7. A sheet according to claim 3 in which said yellow pigment contains iron oxide ochre; said brown pigment contains about one part by weight iron oxide ochre, about two parts by weight red oxide and about 0.4 parts by weight black oxide; said blue pigment contains about two parts by weight black oxide and 0.2 parts by weight blue dye; and said opaque white pigment contains titanium dioxide; and said vehicle is comprised of a methylmethacrylate polymer composition.

8. A method of coloring a plastic dental filling material using a sheet according to claim 1 to provide a natural color matching the tooth to be filled, said material of the type formulated from two components comprising a base material and a catalyst, said method comprising the steps of contacting a preselected number and quantities of said pigments with one of said components and mixing the same to produce a preselected color therein, then adding the other of said components to the mixture and thoroughly mixing said components and pigments to produce a filling material of the desired color.

9. A pad containing a plurality of severable sheets according to claim 1.

* * * * *